US009445748B2

(12) United States Patent
Eichler (10) Patent No.: US 9,445,748 B2
(45) Date of Patent: Sep. 20, 2016

(54) DEVICE AND METHOD FOR FRACTIONALLY COLLECTING CONTENTS OF EXHALED AIR (75) Inventor: Ruediger Eichler, Zellingen (DE)

(73) Assignee: MTI Medtech Innovation GmbH, Zellingen (DE)

( * ) Notice: Subject to any disclaimer, the term of this patent is extended or adjusted under 35 U.S.C. 154(b) by 982 days.

(21) Appl. No.: 13/497,888

(22) PCT Filed: Sep. 29, 2010

(86) PCT No.: PCT/DE2010/001161
§ 371 (c)(1),
(2), (4) Date: Mar. 23, 2012

(87) PCT Pub. No.: WO2011/038726
PCT Pub. Date: Apr. 7, 2011

(65) Prior Publication Data
US 2012/0277617 A1 Nov. 1, 2012

(30) Foreign Application Priority Data

Sep. 30, 2009 (DE) .................. 10 2009 048 644
Sep. 30, 2009 (DE) .................. 20 2009 013 577 U (51) Int. Cl.
A61B 5/08 (2006.01)
A61B 5/097 (2006.01)
G01N 33/497 (2006.01)

(52) U.S. Cl.
CPC ............ A61B 5/097 (2013.01); G01N 33/497 (2013.01)

(58) Field of Classification Search
USPC ....................................................... 600/543
See application file for complete search history.

(56) References Cited

U.S. PATENT DOCUMENTS

| 7,364,553 | B2 | 4/2008 | Paz et al. | |
|---|---|---|---|---|
| 7,779,840 | B2 | 8/2010 | Acker et al. | |
| 2004/0162500 | A1* | 8/2004 | Kline | A61B 5/097 600/532 |
| 2005/0137491 | A1* | 6/2005 | Paz et al. | 600/543 |

(Continued)

FOREIGN PATENT DOCUMENTS

| DE | 19718925 A1 | 10/1998 |
|---|---|---|
| DE | 19755471 A1 | 6/1999 |
| DE | 102007028831 A1 | 12/2007 |

(Continued)

OTHER PUBLICATIONS

Translation of International Preliminary Report on Patentability dated Apr. 12, 2012.

Primary Examiner — Michael Kahelin
Assistant Examiner — Mitchell E Alter
(74) Attorney, Agent, or Firm — Patent Central LLC; Stephan A. Pendorf (57) ABSTRACT A device for fractionally collecting contents of exhaled air by changing the state of matter of the contents by means of the Joule-Thomson effect arising during the expansion of pressurized gas. The temperature of the exhaled air conducted in a flow channel is lowered, because of the cooling of the expanding gas, to a temperature that is suitable for condensing the contents in the exhaled air flow. This device and method provides a more efficient means by which condensate can be separated from exhaled air in comparison to conveying exhaled air along a cooling surface for the condensation of the contents, as a result of which condensation of the contents occurs only in the area of these cooling surfaces, so that several breath cycles are required for the collection of sufficient condensate for analysis.

7 Claims, 3 Drawing Sheets

(56) References Cited

U.S. PATENT DOCUMENTS

2010/0236341 A1* 9/2010 Martin .................. G01N 1/405
73/863.12

FOREIGN PATENT DOCUMENTS

| | | |
|---|---|---|
| EP | 0759169 B1 | 1/1998 |
| WO | 9531721 A1 | 11/1995 |

* cited by examiner

DEVICE AND METHOD FOR FRACTIONALLY COLLECTING CONTENTS OF EXHALED AIR

The invention relates to a device as well as a method for fractionally collecting contents of exhaled air by changing the state of matter of the contents, such as condensation or freezing out, by means of the Joule-Thomson effect, which arises during the expansion of pressurized gas.

Breath condensate contains diverse markers and mediators that reflect the composition of the bronchoalveolar, extracellular epithelial lining fluid. These substances reflect changes due to oxidative damage and infections in the lung, as well as the effect of treatment, so that they play an important role in regard to the diagnosis and monitoring of lung diseases.

Breath condensate collectors are known from prior art.

The German patent application DE 10 2007 028 831 A1, for example, describes a breath condensate sampler in the form of a U-shaped condensation tube with a cooling sleeve that is cooled with a cooling device. The condensed breath condensate runs into a condensate separator, and is conveyed from there into a condensate collecting container. Once an amount of condensate sufficient for analysis is reached, the collecting container is removed and the condensate is fed to a diverse array of analysis methods.

A breath condensate separator is known from the German patent application DE 197 18 925 A1 that consists of a fiber fleece that is disposed after a cooling surface or on a cooling surface. A first fraction of the contents, which consists primarily of water vapor, condenses out on the cooling surface. The aerosols of the contents separate out as a second fraction primarily in the fiber fleece. The contents that are contained in the fiber fleece in the form of aerosols are isolated by means of centrifugation, vacuum, pressurized gas, or elution. The fractions are subsequently analyzed.

DE 197 55 471 A1 discloses an arrangement for catching substances of the exhaled air that has a cooling trap for the separation of the substances present in the exhaled air; said arrangement is disposed at an angle to the flow channel and has an adsorption vessel that is disposed at the end of the flow channel.

A device for the collection of breath condensate is described in EP 0 759 169 B1 that has a sample collection tube that is enclosed by a cooling sleeve, and a collection vessel that is attached at the end of the sample collection tube and on the wall of which the breath condensate freezes out.

It is a disadvantage of the breath condensate collectors named under prior art that the exhaled air has to be conveyed along a cooling surface for the condensation of the contents, as a result of which condensation of the contents occurs only in the area of these cooling surfaces. As a consequence only minor amounts of breath condensate are separated out, with the result that the patient is required to complete several breath cycles for the collection of an amount of breath condensate that is sufficient for the subsequent analysis.

It is therefore the object of the invention to provide a device and a method, by means of which the separation of breath condensate from the exhaled air can be performed more efficiently.

The aforesaid object is achieved by means of a device for fractionally collecting contents of exhaled air by changing the state of matter of the contents by means of the Joule-Thomson effect arising during the expansion of pressurized gas, containing a flow channel through which the exhaled air is conducted, as well as a pressure vessel having at least one expansion nozzle connected to the pressure vessel, the pressure vessel containing a pressurized gas or gas mixture. Due to the expansion of the gas into the flow channel, the temperature of the exhaled air conducted in the flow channel is lowered, because of the cooling of the expanding gas (Joule-Thomson effect), to a temperature that is suitable for condensing the contents in the exhaled air flow that are to be fractionated and/or freezing out said contents in the form of frozen particles. Likewise both states of matter can exist next to each other.

The device furthermore contains a collecting device for receiving the liquid and/or frozen particles (4) conducted along in the exhaled air flow, wherein the collecting device is disposed downstream of the expansion nozzle (3).

Contents of the exhaled air are in particular markers or mediators of airway diseases, such as $H_2O_2$, eicosanoids, such as isoprostane, prostaglandin, leukotrienes, proteins and cytokines, products of lipid oxidation, vasoactive peptides and amines, nitrate, nitrite, s-nitrosothiol, nitrotyrosine and electrolytes.

The pressurized gas or gas mixture can be in liquified form in the pressure vessel. The gas can be a dry gas, preferably a pure gas, in particular argon, nitrogen, carbon dioxide, a hydrocarbon, in particular propane, butane, pentane, or chloroethane. The gas mixture can be a dry gas mixture, preferably a mixture of the named pure gases, in particular consisting of hydrocarbons. In the case of hydrocarbon mixtures, propane, butane, pentane and/or chloroethane are preferred as mixtures.

An expansion nozzle can also be a throttle.

In the case of the expansion cooler that is based on the Joule-Thomson effect, the pressurized working gas is expanded by means of a throttle or a nozzle, and the escaping and, due to the isenthalpic expansion, cooling gas is used to lower the temperature of the exhaled air flow that is flowing through the flow channel. Using this effect the exhaled air is cooled to the extent that the contents to be fractioned condensate or freeze out. The degree of cooling-off in that context depends on the content to be separated, and its phase transition temperature. Corresponding considerations apply of course also for mixtures.

The expansion of the pressurized gas or gas mixture into the exhaled air flow has the effect that the entire exhaled air flow is evenly cooled-off across its entire cross section. This has the effect that the condensation and/or the freezing out of the contents takes likewise place across the entire cross section of the exhaled air flow. In contrast to prior art, the condensation or the freezing out of the contents to be fractioned takes therefore place directly in the exhaled air flow and not at or on a cooled surface. A further difference compared to prior art is the fact that the liquid or frozen particles continue to be conducted along in the exhaled air flow after the change in the state of matter.

This constitutes a significant advantage relative to the condensate separators known from prior art, where condensation only takes place in that partial volume flow that comes in contact with the cooling surface. In the case of prior art a large portion of the contents is released to the surrounding air with the remaining, uncooled breath air flow. In order to obtain a representative average value of the composition and the amount of the individual contents, it is therefore necessary in the case of prior art to collect condensates from several breaths and to combine them for analysis.

These disadvantages are overcome with the present invention. By cooling the entire exhaled air flow, the amount of separable liquid or frozen breath condensate per unit volume of exhaled air can be increased relative to known prior art.

As a consequence fewer breath cycles, or in the best case one breath, are/is necessary in order to separate on the one hand an amount that is representative of the state of the lung, and on the other an amount of breath condensate that is sufficient for the analysis.

The result is that the measurement accuracy is increased and the assessment of the state of the airways is improved.

The increase in efficiency of the condensate separation has furthermore the effect that the patient has to breathe less frequently into the condensate separator, which alleviates the burden on the patient in view of the limitation due to his airways illness.

The flow channel in particular has a geometry that is suitable for inducing flow conditions in the flow channel due to which a separation of the liquid and/or frozen particles conducted along in the exhaled air flow takes place in the collecting device.

The term "geometry of the flow channel" encompasses the construction-technical parameters and dimensions of the components of the device that induce the flow behavior of the exhaled air as well as of the liquid or solid breath condensate in the flow channel. This includes parameters such as the diameter and length of the flow channel, as well as the number, position, and curvature radii of the arches or curvatures. Cross sectional changes, such as constrictions or enlargements, likewise affect the flow. All of these parameters determine the flow response of the exhaled air conducted along in the flow channel or of the liquid or solid breath condensate that is more inert as compared to the gas phase.

In the case of the device according to the invention, provision is now made to separate the droplets or ice particles, based on their inertia, from the gaseous phase by means of the geometry of the prescribed flow conditions, utilizing the principle of inertia after the condensation or the freezing out of the breath condensate. To that end the collecting device is arranged in the flow channel at a location where the liquid and/or solid components are conducted out of the multi-phase flow due to centrifugal and/or gravitational forces.

A simple form of a collecting device is a baffle plate. In the case of a baffle plate, the exhaled air flow that is loaded with liquid droplets or ice particles is guided against a plate in such a manner that the exhaled air flow changes direction. Because of inertia the liquid or frozen particles contained in the exhaled air flow maintain their direction, impinge on the plate, and are diverted from there, preferably directly onto the sensor. A different type of inertial separation utilizes centrifugal forces. In this case the exhaled air flow is guided along a curved path. Due to the centrifugal forces the droplets or ice particles are guided on an outer path with a curvature radius that is as large as possible. This concentrates the droplets or ice particles in this outer range. The droplets or ice particles can then be separated, for example at a sliding surface along the outer range of the exhaled air flow.

In a preferred embodiment the flow channel features a curvature that preferably has a curvature radius from 45 to 90 degrees. The simplest construction provides for a curvature of 90° that produces a redirection of the exhaled air flow by 90°, wherein the collecting device is then arranged at a location of the flow channel wall at which the particles that are conducted out of the exhaled air flow would impinge on the wall of the flow channel.

In particular the collecting device is arranged in the flow channel along the flow direction and opposite the inflow aperture. As a result the redirection of the exhaled air flow takes place directly in front of the collecting device, preferably by 90°. In that context the geometry of the flow channel can be such that the exhaled air flow is divided before the collecting device, and a redirection of a partial exhaled air flow takes place by respectively 90°, preferably in a direction opposite to that of the other partial exhaled air flow.

The collecting device can also be arranged directly in the curvature of the flow channel.

The collecting device can be implemented as a drainage element. In the case of the drainage element, a gas flow loaded with liquid droplets is conveyed through a net-like and/or porous drainage structure. A wire web or a fleece, made for example of plastic or glass fiber, can for example be used as a drainage structure. The breath condensate as droplets or ice particles flows through the drainage structure slower than the exhaled air flow. Due to gravity the droplets move to the geodetically lower area of the drainage structure, collect there, and can be redirected to the sensor.

The collecting device can be aligned in a plane at an angle between 0° and 90° to the horizontal plane, in particular horizontally or vertically to said plane. The angle of the collecting device to the horizontal plane (angle plane) that is established is the result of the liquid or frozen breath condensate's flow response that is induced by the geometry of the flow channel. The incidence angle of the particles on the collecting device can be determined, depending on the flow response of the particles to be separated, via the angle plane of the collecting device. An incidence angle of 90° is preferred, meaning the particles impinge vertically onto the collecting device. Preferably the angle relative to the horizontal is adjustable (manually or electronically), and can therefore be adjusted to the flow response of the particles.

In a first embodiment the expansion nozzle can be arranged directly in the flow channel in order to assure an even cooling-off of the exhaled air flow. In this case the exhaled air circulates around the expansion nozzle. The expansion of the pressurized gas preferably takes place along the longitudinal central axis of the flow channel, so that a cooling-off of the exhaled air flow takes place, originating from the longitudinal central axis in the direction of the wall.

In a second embodiment the expansion nozzle can be arranged in the wall of the flow channel, preferably as a concentric nozzle. In this case the exhaled breath flow is cooled off, originating from the edge area in the direction of the longitudinal central axis of the exhaled air flow.

The expansion nozzle and/or the expansion nozzles can, in both alternatives, be aligned in the flow direction, perpendicular to the flow direction, and/or against the flow direction. Depending on the alignment of the expansion nozzle, the expansion of the gas will contribute to the acceleration or the reduction of the flow, as well as lead to the turbulence of the exhaled air flow and therefore to the generation of a turbulent flow.

In a particular embodiment a flow controller with regulation and control capability is provided that permits adjusting the flow of the expanding gas or gas mixture through the expansion nozzle and adapting it to the flow velocity of the exhaled air in the flow channel. The degree of turbulence of the exhaled air flow, its flow velocity, as well as the process of condensation or ice formation can hereby be significantly influenced and determined. Correspondingly it is possible to respond to the variances in exhalation of a patient who does not exhale regularly. Likewise it is possible to respond to temperature variances of different exhaled air flows by means of the flow controller with regulation and control capability. It is understood that the device, for the purposes of control and regulation of the components, is equipped with a central control and regulator unit, a processor, which processes and controls the system data.

Preferably at least one temperature sensor, which is connected with the processor, is disposed in addition in the wall of the flow channel or directly in the flow channel for measuring the temperature of the exhaled air flow. The temperature value of the exhaled air flow that is determined by the temperature sensor is passed on to the processor. The temperature can also be measured using a non contact IR temperature sensor (infrared temperature sensor). The processor determines, based on the determined temperature values, those operational settings of the flow controller with which the exhaled air flow can be cooled below the dew point or the freezing point of the gas composition of the exhaled air flow, through the expansion of the pressurized gas.

In a further embodiment the device has a temperature-controlled collecting device, wherein the collecting device features a temperature control element by means of which the temperature of the collecting device can be set, controlled, and/or regulated. The collecting device is heated or cooled by means of the temperature control element, depending on the process step or the conditions in the flow channel. The cooling of the collecting device to a temperature of, for example, below the freezing point during the separation prevents separated liquid or frozen breath condensate from being entrained by the exhaled air flow because it freezes to the collecting device. Likewise the re-thawing of the frozen breath condensate and transition into the gas phase are prevented.

After separation the collecting device can be heated up in order to thaw out the separated breath condensate or, in a further step, to heat it up to the analysis temperature. Provision for heating to the analysis temperature is made when the collecting device is connected directly to a sensor, or itself is the sensor measurement surface.

The collecting device can be disposed directly in the flow channel or in or on the wall of the flow channel. Preferably it is connected with the device in a releasable manner, so that it can be removed. The breath condensate separated in the collecting device can then be made available to external analysis methods. Since provision is made that the collecting device can be used simultaneously for analytics, various modified collecting devices can be used in the device. Provision is made here, for example, for modifications of a chemical, biochemical, or physical-chemical form, such as coatings that only bind or convert certain contents, enzymatic coatings or also ab- or adsorptive coatings, reaction solutions, or other compounds or substances that bind the contents. The enumeration is not limiting, but encompasses all modifications that are used in the area of verification analytics. In particular, provision is made to modify the collecting device in such a manner that the conductivity of the breath condensate is increased through the uptake of salts and adjusted for the determination by means of the corresponding sensors.

Preferably the collecting device represents the measurement surface of a sensor. The breath condensate can thereby be analyzed directly after its separation, without having to be removed from the device.

The collecting device can also be connected with the sensor in such a manner that the fractioned contents can be guided onto the measurement surface of the sensor in liquid and/or frozen form. Constructive measures in this context are conduits and in particular sliding surface, by means of which the breath condensate is guided onto the sensor surface. In the case of an improved construction the collecting device is disposed directly on the measurement surface of the sensor. Preferably the collecting device is provided with a layer that stores the contents to be fractioned, for example a layer that draws in or absorbs. Possible storage media are simple webbings, fleeces, foams, but also super absorbers or gels.

In spirometry pneumotachographs are commonly used. Meanwhile pneumotachographs that can be used to analyze the contents of exhaled air are also available in retail. The intent is that the device according to the invention is used in connection with a pneumotachograph or another lung function analysis device. To this end the device according to the invention has, at the opening on the entry side of the device, means for connection with the exhaust opening of the corresponding lung function diagnostics device. In the simplest form this is a plug-in connection in the form of an open pipe end that is slid on or plugged into the exhaust opening. The plug-in connection can be conical or cylindrical, and it can be equipped with O-ring seals. Likewise threaded connectors, bayonet catches, or other releasable connections, such as clamp or click connectors, are provided.

In order to, among other things, prevent a separation of the liquid or solid breath condensate on the wall of the flow channel, a temperature-controllable layer can be provided on or in the wall of the flow channel, by means of which the wall of the flow channel can be heated or cooled. Likewise the flow channel can be temperature controlled by means of the temperature-controllable layer.

Furthermore the invention claims a method for fractionally collecting contents of exhaled air by changing the state of matter of the contents by means of the Joule-Thomson effect arising during the expansion of pressurized gas. In this case the temperature of the exhaled air conducted in the flow channel is lowered due to the expansion of a gas or a gas mixture into a flow channel, to a temperature at which the contents in the exhaled air flow that are to be fractioned condense and/or freeze out in the form of frozen particles in the exhaled air flow. The contents to be fractioned are conducted along after the freezing out as liquid and/or frozen particles in the exhaled air flow, and are separated in a collecting device based on the geometry of the flow channel and the resulting flow conditions in the flow channel.

The method can, in addition, have the method step that during the fractionation of the contents due to their condensation and/or freezing out in the exhaled air flow, and their separation in or on the collecting device, a cooling of the collecting device to 0° C. takes place.

In addition a method step can be provided such that during the fractionation of the contents to be separated through their condensation and/or freezing out in the exhaled air flow, and their separation in or on the collecting device, a modification of temperature, preferably a heating, takes place in the temperature-controllable layer disposed in the wall of the flow channel.

Preferably the method according to the invention encompasses the method step wherein, after the separation of the frozen particles conducted along in the exhaled air flow in the collecting device, the collecting device is heated up to a temperature >0° C., preferably to a sensor-specific operating temperature of the sensor, and in particular to a temperature from 10° C. to 40° C.

The term "sensor-specific operating temperature" describes the temperature range in which the sensor is operated during measurement operation. The temperature depends on the type and functionality of the sensor being used. The invention provides for the use of all common sensors that can be used in sample analytics.

The method can also encompass the method step wherein the duration of the gas expansion, the expansion volume and/or the temperature of the exhaled air flow that is effected by the expansion of the gas or gas mixture is controlled and/or regulated, wherein preferably the measure and the duration of the expansion are dependent on the flow and/or the temperature of the exhaled air flow and/or a defined fraction of the exhaled air flow.

The method provides in a special embodiment additionally the method step that the fractioned and separated contents are determined qualitatively and/or quantitatively. This can take place by means of a sensor that is part of the device or by means of external analytics.

In what follows the invention is further explained based on three embodiments.

In the figures,

FIG. 1 shows a first embodiment of the device for fractionally collecting contents of the exhaled air. The exhaled air of the patient is guided through the opening 9 on the entry side into the flow channel 1, in which the exhaled air is conducted further. The opening 9 on the entry side is implemented as an expanded pipe ending as a means for connection 14, which can be slid onto the exhaust side opening of a lung function diagnostics device (not shown). An expansion nozzle 3 is provided in the flow channel 1 on its longitudinal axis, and exhaled air flow circulates around it. The expansion nozzle is connected via a conduit with a pressure vessel 2 that contains pressurized dry gas or a dry gas mixture. A flow controller 7 is disposed in the conduit between the expansion nozzle 3 and the pressure vessel 2, by means of which the flow of the expanding gas or gas mixture through the expansion nozzle 3 can be set and can be adapted to the flow velocity of the exhaled air in the flow channel 1. While the exhaled air flow (arrow) circulates around the expansion nozzle 3, said expansion nozzle is opened and the gas contained in the pressure vessel 2 expands into the flow channel via the expansion nozzle 3. This effects a cooling-off of the exhaled air flow due to the Joule Thomson effect, which arises during the expansion of pressurized gas.

Figure 1:
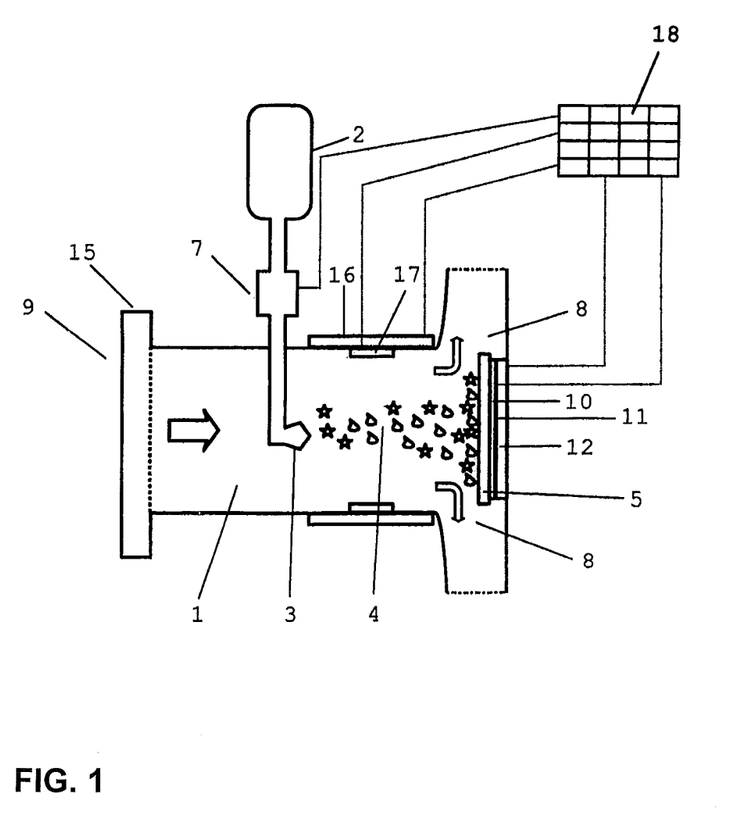
FIG. 1: shows a first embodiment with a parting and a redirection of the exhaled air flow into two opposite directions

Due to the cooling-off of the exhaled air flow to a temperature that is at least below the dew point of the moist exhaled air flow, the breath condensate condenses in the exhaled air flow in the form of droplets or fog. Alternatively the temperature can be lowered below the freezing point of the exhaled air flow. This has the effect that the breath condensate freezes out in the exhaled air flow. Both states of matter can also exist next to each other in the exhaled air flow, depending on the temperature decrease.

After the state of matter change of the breath condensate, it is conducted further along as a fog, droplets, or in the form of ice particles or ice crystals 4 in the exhaled air flow.

The geometry of the flow channel 1 is implemented T-shaped, and has two exhaust openings that face one another. The curvature radius 8 of the flow channel 1 in the T area is respectively 90°.

The wall of the flow channel 1 between the expansion nozzle 3 and the curvature 8 is equipped with a temperature-controllable layer 16 that is disposed for cooling as well as for heating the wall and the flow channel 1.

The collecting device 5, for receiving the liquid and/or frozen particles 4 that are conducted along in the exhaled air flow, is disposed on the wall downstream of the expansion nozzle 3 and opposite the opening 9 on the entry side in a rectilinear extension of the entry-side area of the flow channel. Directly in front of the collecting device 5, the exhaled air flow is split and respectively redirected by 90° due to the curvature of the flow channel 1.

Due to inertia the liquid and/or frozen particles 4 almost maintain their rectilinear flow direction in the exhaled air flow despite its redirection by 90°, and impinge onto the collecting device 5, where they are separated. The collecting device 5 is arranged vertically.

The collecting device 5 is equipped with a temperature control element 10 that is configured for cooling or heating of the collecting device. The sensor 12 is disposed behind the collecting device 5. The measurement surface 11 of the sensor 12 abuts over its entire surface against the collecting device 5, so that the liquid and/or frozen particles 4 are conveyed directly from the collecting device 5 onto the measurement surface 11 of sensor 12, and can be qualitatively and quantitatively determined there.

A non-contact temperature sensor 17 is provided in the wall of the flow channel 1 for the purpose of measuring the temperature of the exhaled air flow, and is connected with a processor 18. The temperature of the exhaled air flow that is determined by temperature sensor 17 is passed on (dotted-dashed line) to the processor 18 in the form of a measured signal, and processed there. The processor 18 generates, on the basis of the measured signal, among other things control signals for the control and regulation of the flow controller 7, for the control and regulation of the temperature control element 10, for the control and regulation of the sensor 12 and/or its measurement surface 11 and/or for the control and regulation of the temperature-controllable layer 16.

Figure 2:
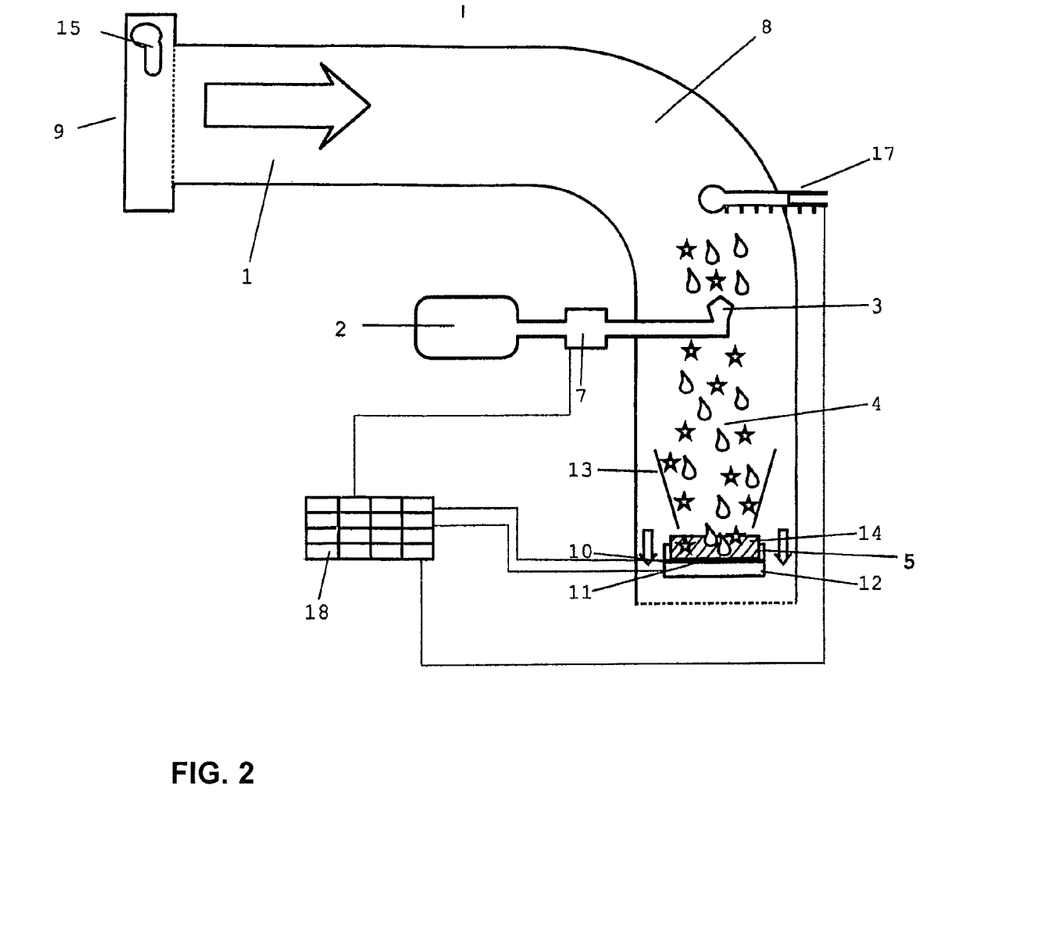
FIG. 2: shows a second embodiment with a redirection of the exhaled air flow by 90° and a separation by means of gravity

FIG. 2 shows a second embodiment of the device. The exhaled air of the patient is guided through the opening 9 on the entry side into the flow channel 1, in which the exhaled air is conducted further. The opening 9 on the entry side is implemented with a bayonet catch as a means for connection 14, which can be threaded on the exhaust side opening of a lung function diagnostics device (not shown).

The geometry of the flow channel 1 provides for a curvature 8 of the flow channel with a curvature radius of 90°. By these means the horizontal flow direction of the exhaled air flow is redirected into a vertical flow direction.

An expansion nozzle 3 is provided in the flow channel 1 after the curvature 8 on its longitudinal axis, and exhaled air flow circulates around it. The expansion nozzle is aligned in a direction opposite to the flow direction and it is connected via a conduit with a pressure vessel 2 that contains a pressurized dry gas or a dry gas mixture. A flow controller 7 is disposed in the conduit between the expansion nozzle 3 and the pressure vessel 2, by means of which the flow of the expanding gas or gas mixture through the expansion nozzle 3 can be set and can be adapted to the flow velocity of the exhaled air in the flow channel 1.

The collecting device 5, for receiving the liquid and/or frozen particles 4 that are conducted along in the exhaled air flow, is disposed in the flow channel downstream of the expansion nozzle 3 and in a rectilinear extension of the exhaust-side area of the flow channel. The collecting device 5 is arranged horizontally.

While the exhaled air flow (arrow) circulates around the expansion nozzle 3, said expansion nozzle is opened and the gas contained in the pressure vessel 2 expands into the flow channel via the expansion nozzle 3. This effects a cooling-off of the exhaled air flow due to the Joule Thomson effect, which arises during the expansion of pressurized gas. Due to the cooling-off of the exhaled air flow, the breath condensate contained in the exhaled air flow condenses in the form of fog or droplets and/or freezes out in the form of ice crystals or ice particles, depending on the degree of cooling of the exhaled air flow.

The liquid and/or frozen particles 4 are subsequently conducted further along in the gaseous portion of the exhaled air flow. The separation of the liquid and/or frozen particles 4 takes place due to their inertia and gravity in the collecting device 5.

The gaseous portion of the exhaled air flow is diverted around the collecting device 5 on the wall side.

The collecting device 5 is equipped with sliding surfaces 13, by means of which the fractioned contents 4 can be guided in liquid and/or frozen form onto the measurement surface 11 of sensor 12. The sliding surfaces 13 can be designed, for example, in the form of a funnel or as an inverted pyramid.

The collecting device 5 is equipped with a temperature control element 10 that is configured for cooling or heating of the collecting device. The sensor 12 is disposed behind the collecting device 5. The measurement surface 11 of the sensor 12 abuts over its entire surface against the collecting device 5, so that the liquid and/or frozen particles 4 are conveyed directly from the collecting device 5 onto the measurement surface 11 of sensor 12, and can be qualitatively and quantitatively determined there.

The collecting device 5 is additionally equipped with a layer 14 that stores the contents 4 to be fractioned, said layer being in direct contact with the measurement surface 11 of the sensor 12.

A temperature sensor 17 is provided in the flow channel 1 for the purpose of measuring the temperature of the exhaled air flow, and is connected with a processor 18. The temperature of the exhaled air flow that is determined by the temperature sensor 17 is passed on (dotted-dashed line) to the processor 18 in the form of a measured signal, and processed there. The processor 18 generates, on the basis of the measured signal, among other things corresponding control signals for the control and regulation of the flow controller 7, for the control and regulation of the temperature control element 10 and/or for the control and regulation of the sensor 12 and/or its measurement surface 11.

Figure 3:
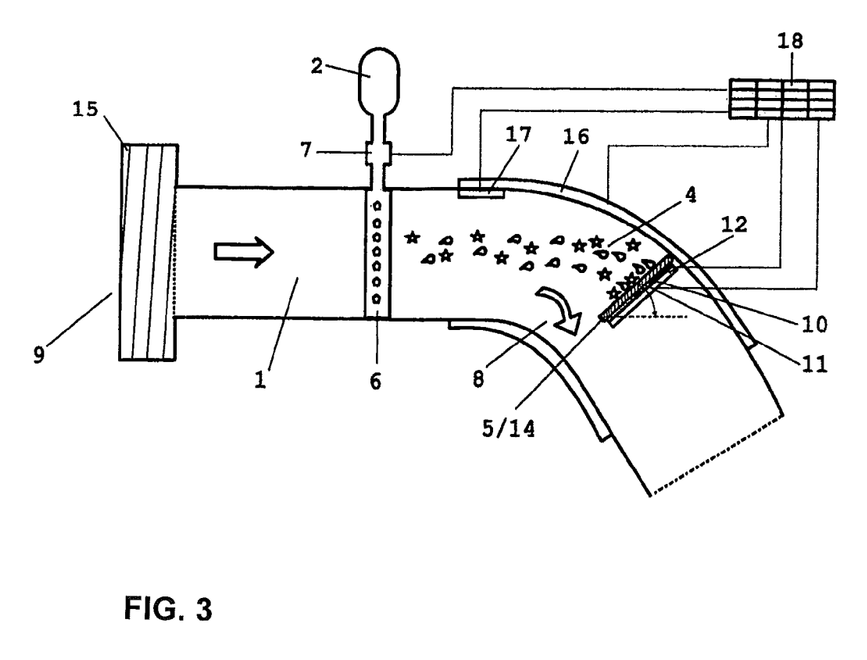
FIG. 3: shows a third embodiment with a redirection of the exhaled air flow by approx. 45° and a separation by means of gravity and centrifugal force

In FIG. 3 a third embodiment of the device is shown.

The exhaled air of the patient is guided through the opening 9 on the entry side into the flow channel 1, in which the exhaled air is conducted further. The opening 9 on the entry side is implemented with a thread as a means for connection 14, which can be threaded onto the exhaust side opening of a lung function diagnostics device (not shown). The thread can be an internal or an external thread.

The geometry of the flow channel 1 provides for a curvature 8 of the flow channel with a curvature radius of 45°. By these means the horizontal flow direction of the exhaled air flow is redirected by 45°.

An expansion nozzle 3 in the form of a concentric nozzle 6 is provided in the flow channel 1 in its wall and before the curvature 8, and exhaled air flow circulates around it. The expansion nozzle 3 of the concentric nozzle 6 is perpendicularly to the flow direction and it is connected via a conduit with a pressure vessel 2 that contains a pressurized dry gas or a dry gas mixture. A flow controller 7 is disposed in the conduit between the expansion nozzle 6 and the pressure vessel 2, by means of which the flow of the expanding gas or gas mixture through the expansion nozzle 6 can be set and can be adapted to the flow velocity of the exhaled air in the flow channel 1.

The collecting device 5, for receiving the liquid and/or frozen particles 4 that are conducted along in the exhaled air flow, is disposed in the flow channel 1 downstream of the concentric expansion nozzle 6 in the curvature 8 of the flow channel 1. The collecting device 5 is aligned at a variably adjustable angle to the horizontal plane. The angle of the collecting device 5 is adjustable (dotted-dashed line) within an angle range from 20° to 70°, preferably from 30° to 60°, and in particular from 40° to 50°.

While the exhaled air flow (arrow) circulates around the concentric expansion nozzle 6, said concentric expansion nozzle is opened and the gas contained in the pressure vessel 2 expands into the flow channel via the concentric expansion nozzle 6. This effects a cooling-off of the exhaled air flow due to the Joule Thomson effect, which arises during the expansion of pressurized gas. Due to the cooling-off of the exhaled air flow, the breath condensate contained in the exhaled air flow condenses in the form of fog or droplets and/or freezes out in the form of ice crystals or ice particles, depending on the degree of cooling of the exhaled air flow.

The liquid and/or frozen particles 4 are subsequently conducted further along in the gaseous portion of the exhaled air flow. The separation of the liquid and/or frozen particles 4 takes place according to the principle of inertia as a result of their inertia and gravity in the collecting device 5.

The gaseous portion of the exhaled air flow is diverted around the collecting device 5 on the wall side.

The collecting device 5 is additionally equipped with a layer 14 that stores the contents 4 to be fractioned, said layer being in direct contact with the measurement surface 11.

The collecting device 5 is equipped with a temperature control element 10 that is configured for cooling or heating of the collecting device. The sensor 12 is disposed behind the collecting device 5. The measurement surface 11 of the sensor 12 abuts over its entire surface against the collecting device 5, so that the liquid and/or frozen particles 4 can be conveyed directly from the collecting device 5 onto the measurement surface 11 of sensor 12, and can be qualitatively and quantitatively determined there.

A temperature sensor 17 is provided in the wall of the flow channel 1 for the purpose of measuring the temperature of the exhaled air flow, and it is connected with a processor 18. The temperature of the exhaled air flow that is determined by the temperature sensor 17 is passed on (dotted-dashed line) to the processor 18 in the form of a measured signal, and is processed there. The processor 18 generates, on the basis of the measured signal, among other things control signals for the control and regulation of the flow controller 7, for the control and regulation of the temperature control element 10, for the control and regulation of sensor 12 and/or its measurement surface 11 and/or of the temperature-controllable layer 16.

The wall of the flow channel 1 is equipped with a temperature-controllable layer 16 that is provided for cooling as well as for heating the wall of the flow channel 1 and/or for the temperature control of the exhaled air flow.

The temperature-controllable layer 16 is located on the interior side of the wall, downstream of the concentric expansion nozzle 6, and extends beyond the curvature 8 of the flow channel 1.

LIST OF REFERENCE NUMERALS

1 Flow channel
2 Pressurized container
3 Expansion nozzle
4 Condensed and/or frozen breath condensate
5 Collecting device
6 Concentric nozzle
7 Flow-through controller
8 Curvature
9 Opening on the entry side
10 Temperature control element
11 Measurement surface of the sensor
12 Sensor
13 Sliding surface
14 Storage layer
15 Means for connection
16 Temperature-controlled layer
17 Temperature sensor
18 Processor

The invention claimed is:

1. A method for fractionally collecting contents of exhaled breath by changing the state of matter of the contents by means of the Joule-Thomson effect arising during the expansion of pressurized gas, comprising:
    exhaling breath into a flow channel (1) in a direction of flow,
    expanding a pressurized working gas or gas mixture from a pressure vessel into the flow channel (1) containing the exhaled breath, whereby the temperature of the working gas or gas mixture as well as the exhaled breath in the flow channel (1) is lowered by means of the Joule-Thomson effect to a temperature at which the contents in the exhaled breath flow that are to be fractionated condense and/or freeze out in the form of frozen particles (4) in the flow of exhaled breath and working gas or gas mixture and the condensate and/or frozen particles are conducted along as liquid and/or frozen particles (4) in the flow of exhaled breath and working gas or gas mixture, and
    separating the liquid and/or frozen particles (4) from the remaining breath and working gas or gas mixture, into a collecting device (5).

2. The method according to claim 1, wherein through the geometry of the flow channel (1), flow conditions are induced in the flow channel (1), due to which the liquid and/or frozen particles (4) are separated directly into the collecting device (5).

3. The method according to claim 1, wherein during the fractionation of the contents (4) and due to their condensation and/or freezing out in the exhaled breath flow, and their separation in or on the collecting device (5), a cooling of the collecting device (5) to ≤0° C. takes place.

4. The method according to claim 1, wherein during the fractionation of the contents (4) to be separated through their condensation and/or freezing out in the exhaled breath flow, and their separation in or on the collecting device (5), a heating takes place in a temperature-controllable layer (16) disposed in the wall of the flow channel (1).

5. The method according to claim 1, wherein after the separation of the frozen particles (4) conducted along in the exhaled breath flow, the collecting device (5) is heated to a temperature >0° C. for purposes of melting the frozen particles in the collecting device (5).

6. The method according to claim 1, wherein a duration of the gas expansion, an expansion volume or the temperature of the exhaled breath flow that is effected by the expansion of the gas or gas mixture is controlled or regulated, wherein the expansion volume and the duration of the expansion are dependent on at least one of the flow and the temperature of the exhaled breath flow or a defined fraction of the exhaled breath flow.

7. The method according to claim 1, wherein the fractionated and separated contents (4) are determined qualitatively and/or quantitatively.

* * * * *